United States Patent [19]
Pronovost et al.

[11] Patent Number: 5,814,455
[45] Date of Patent: Sep. 29, 1998

[54] ANTIGEN PREPARATION FOR DETECTING H. PYLORI

[75] Inventors: Allan David Pronovost, San Diego; Jan Waclaw Pawlak, Cardiff; Kristy S. Condon, San Diego, all of Calif.

[73] Assignee: Quidel Corporation, San Diego, Calif.

[21] Appl. No.: 292,932

[22] Filed: Aug. 18, 1994

Related U.S. Application Data

[63] Continuation of Ser. No. 22,817, Feb. 24, 1993, abandoned, which is a continuation of Ser. No. 621,845, Dec. 4, 1990, abandoned.

[51] Int. Cl.$^6$ .............. G01N 33/53; G01N 33/536; G01N 33/569; C12N 1/00
[52] U.S. Cl. .............. 435/7.1; 435/7.2; 435/7.92; 435/822; 424/184.1; 424/234.1; 514/2
[58] Field of Search .............. 424/234.1; 435/7.1, 435/7.2, 7.92, 822

[56] References Cited

U.S. PATENT DOCUMENTS

| | | | |
|---|---|---|---|
| 4,882,271 | 11/1989 | Evans et al. | 435/7 |
| 4,981,685 | 1/1991 | Healy | 424/92 |
| 5,459,041 | 10/1995 | Blazer et al. | 435/7.21 |

FOREIGN PATENT DOCUMENTS

| | | | |
|---|---|---|---|
| 0329570 | 8/1989 | European Pat. Off. | G01N 33/569 |
| WO 89/09407 | 10/1989 | WIPO | G01N 33/569 |
| WO 90/03575 | 4/1990 | WIPO | C07K 3/20 |

OTHER PUBLICATIONS

Marshall B., et al., "Unidentified curved bacilli in the stomach of patients with gastritis and peptic ulceration" *Lancet* (1984) 1(8390):1311–1314.
Von Wulffen H., in *Campylobacter pylori* (1988), Menge et al., ed., Springer–Verlag, pp. 157–163.
Goodwin C., et al., "Enzyme–linked immunosorbent assay for *Campylobacter pyloridis*: Correction with presence of *C. pyloridis* in the gastric mucosa" *Journal of Infectious Diseases* (1987) 155(3):488–494.
Bolton F., et al., "Evalation of three *Campylobacter pylori* antigen preparations for screening sera from patients undergoing endoscopy" *J. Clin. Pathol.* (1989) 42:723–726.
Chevrier D., et al., "Indentification and classification of Campylobacter strains using nonradioactive DNA probes" *Journal of Clinical Microbiology* (1989) 27(2):321–326.
Luke et al., "Identification of flagellar and associated polypeptides of *Helicobacter* (formerly *Campylobacter*) *pylori*" *FEMS Microbiology Letters* (1990) 71:225–230; and International (PCT) Patent Publication No. WO 90/03575 (5 Apr. 1990).
Abstract of International (PCT) Patent Publication No. WO 90/03575 (5 Apr. 1990).
Hirsch et al., "Comparison of different antigen preparation in an evaluation of the immune response to *Campylobacter pylori*" *Eur. J. Clin. Microbiol. Infect. Dis.* (1988) 7:570–575.
Hirsch et al., "Comparison of ELISA antigen preparations alone or in combination for serodiagnosing *Helicobacter pylori* infections" *J. Clin. Pathol.* (1990) 43:511–513.
Thomas et al., "Purification of membrane proteins" Guide to Protein Purification *Methods in Enzymology* (1990) 182:499–520.
Perez–Perez et al., "Conservation and diversity of *Campylobacter pyloridis* major antigens" *Infect. Immunity* (1987) 55:1256–1263.
Newell "Identification of the outer membrane proteins of *Campylobacter pyloridis* and antigenic cross–reactivity between *C. pyloridis* and *C. jejuni*" *J. Gen. Microbiol.* (1987) 133:163–170.
Megraud et al., "Characterization of '*Campylobacter pyloridis*' by culture, enzymatic profile, and protein content" *J. Clin. Microbiol.* (1985) 22:1007–1010.
Dunn et al., "Two–dimensional gel electrophoresis and immunoblotting of Campylobacter outer membrane proteins" *Infect. Immunity* (1987) 55:1564–1572.
Wenman et al., "Antigenic analysis of Campylobacter flagellar protein and other proteins" *J. Micro. Biol.* (1985) 21:108–112.
Evans et al., "A sensitive and specific serologic test for detection of *Campylobactor pylori* infection" *Gastroenterol.* (1989) 96:1001–1008.
Cover et al., "Characterization of and human serologic response to proteins in *Helicobacter pylori* broth culture supernants with vacuolizing cytotoxin activity" *Infect. Immunity* (1990) 58:603–610.
Perez–Perez et al Inf & Imm 55:1256–1263 May 1987.
Newell et al J of Gen Microbiol. 133:163–170 1987.
Megrand et al J of Clinic. Microb. 22:1007–1010 1985.
Dunn et al Inf & Imm 55:1564–1572 1987.
Thomas et al Methods in Enzymology vol. 182:499–520 1990, Purification of Membrane Proteins.
Hirschl et al Eur J. Clin Microbiol Infect Dis. 7:570–575 1988 Comparision of Different Antigen Preparations in an Evoluation of the Immune Response to *Campylobacter Pylori*.
Hirschl et al J Clin Paltrol 43:511–513 1990 Comparison of ELISH antigen preparations alone or in combination for serodiagnosing *Helicobacter pylori* infections.
Howard et al, Parasitology 88:27–36, 1984.
Stacey et al Eur J. Clin Microbiol Infect Dis 9:732–737, 1990.
Hirsche et al, J. Clin Paltrol 43;511–513, 1990.
Wulffen et al J. Clin Pathol 41:653–659, 1988.
Neugebauer Methods in Enzmology, vol. 182, pp. 239–253, Detergents:An Overview, 1990.

*Primary Examiner*—Hazel F. Sidberry
*Attorney, Agent, or Firm*—Morrison & Foerster

[57] ABSTRACT

A sensitive and specific antigen preparation for the detection of *Helicobacter pylori* in biological samples is disclosed. The preparation uses a range of antigens derived from size exclusion chromatography of detergent-solubilized *H. pylori* cells. Serological assays such as ELISA, latex agglutination, and rapid EIA assays utilizing the improved antigen preparation, and a kit for use in these serological assays are also disclosed.

2 Claims, 1 Drawing Sheet

ANTIGEN PREPARATION FOR DETECTING H. PYLORI

This application is a continuing application of application Ser. No. 08/022,817, filed 24 Feb. 1993 and now abandoned, which is a continuation of application Ser. No. 07/621,845, filed 4 Dec. 1990 and now abandoned.

TECHNICAL FIELD

This invention relates to an antigen preparation that can detect the presence of antibodies specific to *Helicobacter pylori*. In particular, it relates to a mixture of antigens isolated by size exclusion chromatography of detergent-solubilized *H. pylori* antigens. The invention also relates to a method and kit for detecting the presence of the *H. pylori*-specific antibodies.

BACKGROUND ART

*Helicobacter pylori* (formerly known as *Campylobacter pylori*), a bacterium that colonizes the human stomach, was discovered in 1983, as described in B. J. Marshall et al., *Lancet* (1984) I:1311–1314. The association of *H. pylori* with gastric disorders such as chronic active gastritis, gastric and duodenal ulcer disease and non-ulcer dyspepsia has generated a great deal of interest in the gastroenterological medical community.

The precise role of *H. pylori* in peptic ulcer disease has not yet been elucidated. Nevertheless, its relation to gastric disease has caused significant efforts to be directed towards developing methods for detecting the organism in the human stomach. Detection can be accomplished in two ways: (1) directly, by examining a stomach biopsy by histology or cell culture isolation methods or both; or (2) indirectly, by testing a sample of peripheral blood serum for circulating antibodies against *H. pylori*. The simplicity and economy (for both patient and physician) of the latter serological method makes it particularly attractive.

The accuracy of a serological test for antibodies against *H. pylori* depends on the nature of the antigenic preparation that will bind the antibodies. The preparations used in current testing range from whole intact organisms to highly purified material consisting of one major antigenic molecule.

H. Von Wulffen, in *Campylobacter pylori* pp. 157–163, Menge et al., eds., Springer-Verlag (1988), used *H. pylori* crude cell lysates to detect the presence of infections in gastric patients. European Patent Application Pub. No. 0329570 by M. J. Blaser teaches that similar crude cell lysates can be used to detect *H. pylori* antibodies. Acid-glycine extracts of *H. pylori* were used as antigenic preparations in enzyme-linked immunosorbent assays ("ELISAs") as described in C. S. Goodwin et al., *J. Infectious Diseases* (1987) 155:488–494. Surface antigen preparations and urease preparations as well as acid-glycine extracts were used to screen gastric patient sera in F. J. Bolton et al., *J. Clin. Pathol.* (1989) 42:723–726.

These crude preparations have many drawbacks. Using the whole organism or crude lysates often causes problems with the specificity of a serological test. The presence of some undesirable material in the preparation may cause "nonspecific" binding of other antibodies so that individuals who do not have antibodies specifically against *H. pylori* will give a "false positive" test result. False positives can also occur when the preparation contains common antigens shared with other *H. pylori*-related organisms. Persons infected with those organisms can produce antibodies cross-reactive with the *H. pylori* preparation. Thus, a preferred preparation is enriched in highly-reactive species-specific antigens and does not contain significant cross-reacting levels of antigens common to related organisms.

Another drawback of crude preparations is that they often fail to detect the presence of *H. pylori*-specific antibodies. These "false negative" test results may occur when: (1) *H. pylori*-specific antigenic material is not readily available for antibody binding due to interactions with other components in the preparation; (2) the preparation process alters the *H. pylori*-specific antigenic material so that it is less reactive with antibodies; or (3) *H. pylori*-specific antigenic material is too-heavily diluted by the presence of undesirable material.

At the other end of the spectrum of antigen preparations, PCT Application Pub. No. WO 89/09407 teaches the diagnosis of *H. pylori* infections using a preparation of purified *H. pylori* urease. *H. pylori* contains a species-specific urease which can be used in serodiagnosis. Other preparations using material produced from a single cloned *H. pylori* gene may also be employed, e.g., D. Chevrier et al., *J. Clin. Micro.* (1989) 27:321–326.

The use of purified single antigen preparations or cloned gene products eliminates some of the causes of false results listed above. However, the use of a cloned gene preparation may introduce expression-system by-product molecules which may still give false positive test results. In addition, highly purified or cloned gene preparations may produce the relevant antigen in an altered non-native structure that is less reactive with antibodies, giving false negative test results.

Furthermore, Western blot analysis has shown that infected individuals typically produce antibodies to *H. pylori* that recognize several antigens. A preparation containing a single purified antigenic molecule or gene product needlessly limits the scope of antibody recognition and may give false negative results for infected individuals with no or few antibodies to the particular antigen used.

U.S. Pat. No. 4,882,271 to Evans et al. ("Evans") describes a process for obtaining an antigenic preparation that lies between the above extremes: it contains only a few major antigenic components having molecular weights between 300,000 and 700,000 daltons. The Evans preparation is obtained by collecting fractions from a size exclusion chromatography separation in a defined high molecular weight range having significant urease enzyme activity. Evans suggests that although further purification is not necessary, the degree of purification in the disclosed preparations is necessary to provide adequate sensitivity and specificity in assays.

Individuals infected with *H. pylori* in fact respond to many different antigens. Our research indicates that more sensitive and specific tests for antibodies to *H. pylori* can be constructed using the extraction and purification procedures as described herein to produce a superior *H. pylori* antigen preparation, having a broader spectrum of *H. pylori*-specific and reactive antigens, which has not been previously recognized.

SUMMARY OF THE INVENTION

Figure 1:
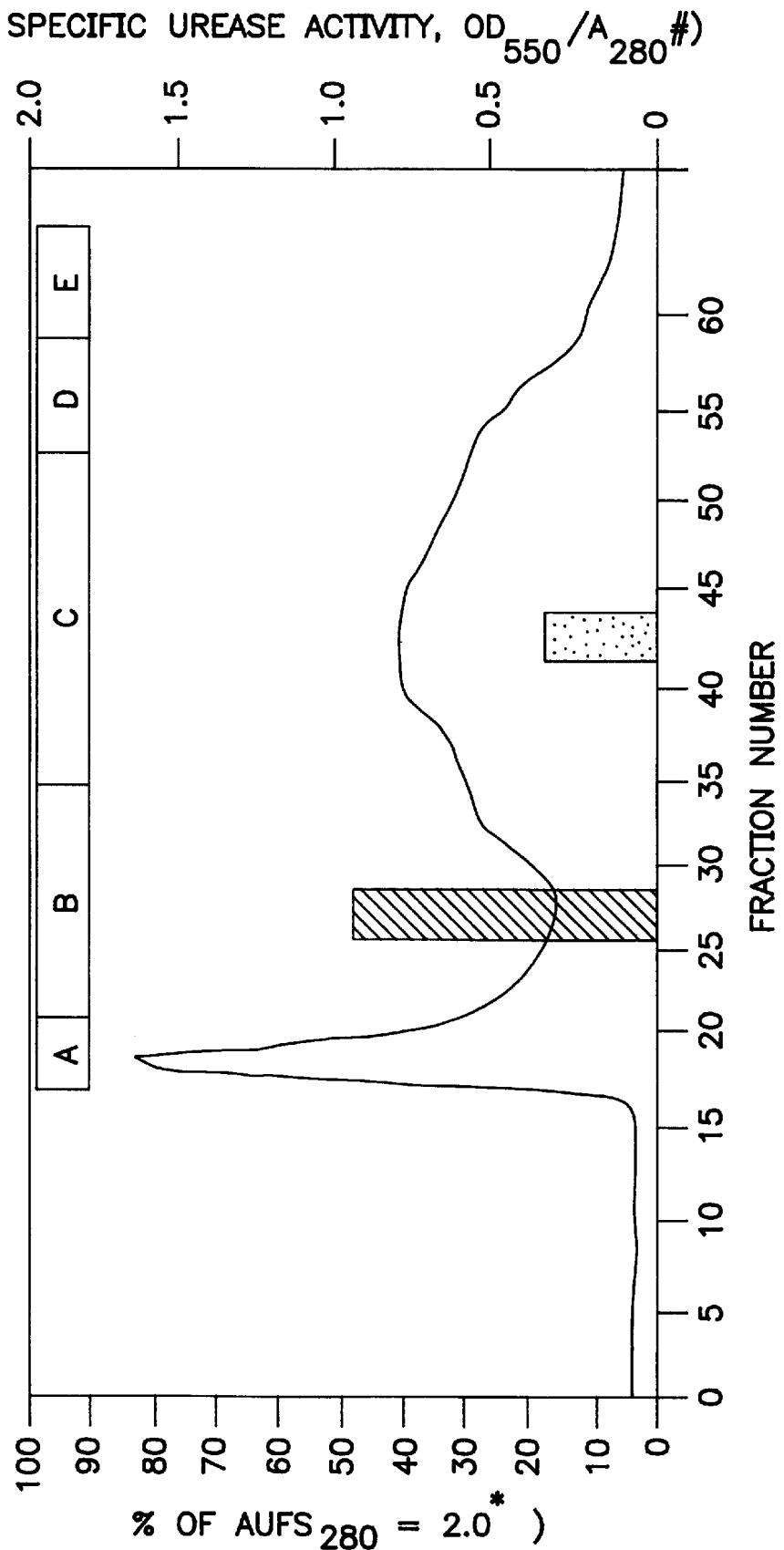
FIG. 1 shows the typical fractionation profile of an n-octyl β-glucopyranoside (BOG) extract of *H. pylori* antigens on a 6FF Sepharose column (a column containing cross-linked agarose beads as gel-filtration medium). Walker and Cox, *The Language of Biotechnology,* American Chemical Society (1988), p. 217., and the urease activity of pooled fractions.

It is accordingly an object of this invention to provide an antigenic preparation incorporating a mixture of antigens from detergent-solubilized *H. pylori* cells, and which is capable of determining the presence or absence of an *H. pylori* infection in a biological sample with a greater degree of accuracy and reliability than previously available.

It is a further object of this invention to provide an antigenic preparation to determine the presence of *H. pylori* infection, where that preparation maximizes the rate of positive response when infection is present by minimizing the rate of false negatives, thereby improving assay sensitivity. Similarly, the preparation maximizes the rate of negative response when infection is absent by minimizing the rate of false positives, thereby improving assay specificity.

It is yet a further object of this invention to provide a method for determining the presence of an *H. pylori* infection in a biological sample with a maximum "signal-to-noise" ratio using an antigen preparation enriched with a broad spectrum of highly reactive *H. pylori*-specific antigens.

It is another object of this invention to provide a kit to be used to determine the presence of an *H. pylori* infection in a biological sample with a maximum "signal-to-noise" ratio.

Additional objects, advantages and novel features of the invention will be set forth in part in the description which follows, and in part will become apparent to those skilled in the art upon examination of the following, or may be learned by practice of the invention.

In one aspect of this invention, a composition comprising purified antigens from cell-associated proteins of *Helicobacter pylori* is provided, the antigens having a molecular weight of about 16,000 to 120,000 daltons as determined by reduced SDS-PAGE analysis, and having urease-depleted activity.

In another aspect of this invention, a composition comprising purified antigens from cell-associated proteins of *Helicobacter pylori* is provided, the composition obtained by: growing *Helicobacter pylori* cells in a broth medium supplemented with 10% fetal bovine serum and harvesting the cells when log phase growth has begun to decline; solubilizing the cells in a phosphate buffered saline solution containing about 1% n-octyl-β-D-glucopyranoside for at least about 30 minutes to obtain a cell protein solution; dialyzing the cell protein solution against PBS overnight, then centrifuging the solution at medium speed to obtain a supernatant; loading the supernatant onto a 6FF-Pharmacia size exclusion column; eluting the column with 50 mM Tris buffer containing 0.025% sodium azide and collecting the eluted fractions; excluding the high molecular weight protein peak containing the majority of urease activity; and pooling the remaining urease-depleted lower molecular weight protein fractions.

In a further aspect of this invention, a method for detecting *Helicobacter pylori* infection in a biological sample is provided, the method comprising: contacting a composition comprising purified antigens from cell-associated proteins of *Helicobacter pylori* obtained by the above-mentioned methods with the sample to form an incubation complex; and testing the incubation complex for the presence of antigen-antibody complexes denoting the presence of *Helicobacter pylori* infection.

In yet another aspect of this invention, a kit to be used in the detection of *Helicobacter pylori* infection in a biological sample is provided, the kit comprising purified antigens from cell-associated proteins of *Helicobacter pylori* obtained by the above-mentioned methods.

DETAILED DESCRIPTION OF THE INVENTION

Definitions:

The "antigens" of this invention are "cell-associated proteins" extracted from *Helicobacter pylori* cells. "Cell-associated proteins" include outer membrane-associated proteins and surface proteins. Cell-associated proteins may be extracted from *H. pylori* cells, without breaking the cells open, by using non-ionic detergents such as n-octyl-β-D-glucopyranoside (BOG), and other detergents performing the same function. These cell-associated proteins are capable of initiating an immune response in the form of antibodies that recognize antigenic determinants on these proteins.

By "biological sample" as used herein is meant a sample of blood, blood serum, plasma, lymphatic or other extract taken from a human patient to be tested for the presence of an *H. pylori* infection.

"High molecular weight urease activity-containing protein fractions", as used herein, refers to chromatographic fractions having a significant absorbance at 280 nm containing proteins with molecular weights generally greater than 300,000 daltons (as determined by sizing column chromatography), and exhibiting significant urease activity. "Low molecular weight urease-depleted protein fractions", as used herein, refers to low molecular weight fractions having significant absorbance at 280 nm and urease-depleted activity.

"Urease-depleted activity", as used herein, refers to a specific activity of less than 0.34 $OD_{550}/A_{280}$ units as measured in the urease-catalyzed urea hydrolysis assay described in Example 2.

The Antigen Preparation:

The antigen preparations of this invention are cell-associated proteins derived from *H. pylori* cells. The cells are solubilized with a non-ionic detergent, and the resultant supernatant is subjected to size exclusion column chromatography, followed by the pooling of selected column fractions. The pooled fractions of this invention do not include those fractions with the majority of significant urease enzyme activity. Instead, a number of fractions containing low molecular weight antigens depleted in urease activity are pooled to obtain the final preparation.

The antigens of this invention may be prepared in a number of ways. In a preferred embodiment, the antigens are prepared by growing *H. pylori* organisms in a growth medium such as Brucella broth. The broth will contain nutrient supplements. A preferred supplement is fetal bovine serum. The cells are incubated in flasks with rotation in a mixed atmosphere of $CO_2$, $O_2$ and $N_2$. The cells are harvested by medium speed centrifugation after log phase growth has begun to decline. *H. pylori* cells may also be grown by plating, as, for example, on blood agar plates, followed by harvesting.

After the *H. pylori* cells have been harvested, they may be washed, and suspended in a buffer for solubilization. In a preferred embodiment, the solubilization buffer is phosphate buffered saline (PBS) containing a non-ionic detergent. Non-ionic detergents include reaction products of ethylene or propylene oxide with: (1) $C_6$–$C_{22}$ alkyl phenols; or (2) aliphatic primary or secondary linear or branched alcohols.

Other non-ionic detergents include long-chain tertiary amine oxides, long-chain tertiary phosphine oxides and dialkyl sulfoxides. In a preferred embodiment, the non-ionic detergent is n-octyl-β-D-glucopyranoside included at a concentration of 0.1–3.0% (wt/vol), most preferably 1.0%.

The washed *H. pylori* cells are suspended in about 0.1 to 10 ml of the solubilization buffer per 100 mg wet weight of cells, more preferably about 1 ml solubilization buffer per 100 mg wet weight of cells. This suspension is incubated and mixed for at least about 30 minutes at room temperature. The resulting solubilized cell suspension is dialyzed against PBS, usually overnight, and a supernatant collected by medium-speed centrifugation.

The resultant supernatant is then subjected to a sizing separation, usually size exclusion column chromatography. In a preferred embodiment, the supernatant is loaded on a 6FF-Pharmacia size exclusion column and then eluted with 50 mM Tris buffer (pH 8.0) containing about 0.025% sodium azide. Fractions are then collected and absorbance at 280 nm as well as urease activity are monitored to determine fractionation profiles.

The high molecular weight urease-activity containing protein fractions having the majority of urease activity are discarded and the remaining low-molecular weight urease-depleted fractions are pooled. This pool constitutes the antigen extract of this invention. The extract consists of antigens having molecular weights less than 200,000 daltons, more particularly from about 16,000 to about 120,000 daltons, as determined by reduced SDS-PAGE analysis. In a preferred embodiment, this extract is made by pooling fractions 34–52 as shown in FIG. 1.

Methods:

A variety of serological assays can be used in this invention to detect antibodies to *H. pylori* in biological samples. Well-characterized assays such as enzyme-linked immunosorbent assays (ELISAs), rapid flow-through assays, latex agglutination assays, immunoblot assays, and lateral flow immunoassays are all contemplated in this invention.

In a preferred embodiment, the serological assay is performed by the EIA microtiter method. In this method, the wells of microtiter plates are coated with the preparations of this invention described above, and incubated overnight at 4° C. The preparation solution is then discarded and the wells are dried for 2 hours at 37° C. Biological samples to be tested are then prepared at various dilutions in PBS containing bovine serum albumin (BSA) and added to the wells. After incubation for 30 minutes at 25° C., the biological sample is removed and the wells are washed with PBS containing the detergent Tween 20. Then an enzyme-conjugated rabbit antibody preparation that recognizes human immunoglobulin G ("anti-human IgG") is added and the wells are further incubated. The solution is again discarded and another PBS-Tween 20 wash is performed. Finally a solution containing a substrate for the conjugated enzyme is added.

If human antibodies to *H. pylori* are present in the biological sample, then the rabbit anti-human IgG antibodies bind to the well and the conjugated enzyme will react with the substrate and produce a color change that reflects the quantity of antibody present. In a preferred embodiment, the enzyme is horseradish peroxidase, and the substrate is 2,2'-azino-bis(3-ethylbenzthiazoline sulfonic acid) (ABTS).

Another immunoassay is the rapid flow-through EIA assay which resembles the EIA microtiter assay but utilizes an antigen preparation adhered to a porous nylon membrane. The nylon membrane is then placed atop an absorbent pad and encased in a plastic holder exposing the membrane. The biological sample is diluted and allowed to flow through the membrane. Then, enzyme-conjugated rabbit anti-human IgG antibodies are allowed to flow through followed by a wash solution. Finally, a solution containing the substrate for the conjugated enzyme is added and color change is produced as in the ELISA method.

In the latex agglutination assay, the antigen preparation is affixed to latex beads. The biological sample is then incubated directly on a slide with the latex particles. In a short time the reaction is examined for the presence of cross-linked, or agglutinated latex particles indicating the presence of antibodies to *H. pylori* antigens.

The Kit:

This invention also contemplates a kit containing an antigen preparation described above. The kit can then be used to perform the methods of this invention described above.

In a preferred embodiment, the kit contains an antigen preparation prepared as described above and then fixed onto a solid support for use in a serological assay.

The following examples are intended to illustrate the invention but not to limit its scope.

EXAMPLE 1

Methods of Growth and Extraction

Growth of *H. pylori*

Brucella broth (Difco Laboratories) supplemented with fetal calf serum was used as a growth medium for *H. pylori* at 35° C. under a mixed atmosphere of $Co_2$, $O_2$, and $N_2$. A 20 ml sample of growth medium was inoculated with 1 ml of frozen *H. pylori* stock, incubated, and expanded to 1 l growth during the next 48 to 72 hours to a cell density of 8 to $10 \times 10^7$ CFU (colony forming units) per ml. Cells were harvested by medium-speed centrifugation, washed with deionized water and packed by medium-speed centrifugation, yielding $1 \times 10^6$ cells per mg of wet cell pellet.

Sonicate Extract From *H. pylori* Cells

The preparation of sonicate antigen extract from *H. pylori* was similar to that described in Perez-Perez et al., *Ann. Int. Med.* 109:11 (1988). Following the initial cell harvest by medium-speed centrifugation, the cells were washed three times with sterile isotonic saline. The final cell pellet was suspended at a concentration of 10 mg (wet weight) of cells per 1 ml of deionized water. A 10 to 15 ml suspension was typically sonicated with ice bath cooling using a Model 300 Sonic Dismembrator (Fisher Scientific Co., Pittsburgh, Pa.) with two 2-minute bursts at maximum microtip power output. The resultant sonicate was frozen at −70° C., then thawed and centrifuged as described above. The supernatant was collected and protein content estimated by reading absorbance at 280 nm.

Glycine Extract of *H. pylori* Cells

The preparation of an acidic glycine extract of antigens was similar to that described for *C. jejuni* in Blaser and Duncan, *Infect. Immun.* 44:292 (1984). Following an initial harvest by medium-speed centrifugation, the cells were washed three times with sterile isotonic saline and suspended at 25° C. in 0.2M glycine-hydrochloride buffer (pH 2.2) at a concentration of 10 mg (wet weight) of cells in 1 ml of buffer. After 15 minutes, the cell suspension was again centrifuged. The supernatant was retained and dialyzed overnight against cold water with 12 to 14 kilodalton molecular weight cut-off tubing. The retentate was collected and protein content estimated by reading absorbance at 280 nm.

n-Octyl-β-glucopyranoside (BOG) Extraction of H. pylori Cells

In a typical experiment, an H. pylori culture was harvested by medium-speed centrifugation and the cells were washed twice by suspending in sterile deionized water followed by centrifugation. The final cell pellet was suspended at a concentration of 100 mg/ml in phosphate-buffered saline (PBS) containing sodium azide and 1% (w/v) n-octyl-β-glucopyranoside (BOG) and incubated at 25° C. for 30 minutes. The suspension was dialyzed overnight at 4° C. with 12–14 kilodalton molecular weight cutoff tubing against PBS containing sodium azide, then centrifuged at medium speed. The supernatant was collected and protein content in the extract determined by absorbance at 280 nm.

EXAMPLE 2

Preparation and Analysis of BOG H. pylori Antigen Extract

The above-described BOG extract was applied to a 6FF-Sepharose resin (Pharmacia) equilibrated in 50 mM Tris-HCl buffer (pH 8.0) containing 0.025% (w/v) sodium azide. Seventy fractions (equal to 2% column volume each) were collected, and monitored by absorbance at 280 nm. A typical fractionation profile of BOG extract is presented in FIG. 1.

The fractionation profile in FIG. 1 reveals five discernible components: (1) Pool A (fractions 17–19 inclusive), representing the first high-molecular weight peak and having negligible H. pylori urease activity; (2) Pool B (fractions 20–33) associated with a "peak valley" and having the majority of urease activity; (3) Pool C (fractions 34–52) containing low molecular weight urease-depleted proteins; (4) Pool D (fractions 53–58) representing the descending slope of the second protein peak; and finally (5) Pool E (fractions 59–63) representing the lower molecular weight trailing edge of the second peak.

The fractions were analyzed by running reduced SDS-PAGE on 0.15×12×15 cm gels [12% w/v acrylamide—0.32% (w/v) N, N-methylenebisacrylamide] in the presence of 0.1% (w/v) SDS. High- and low-molecular weight protein standards (BioRad Labs) were applied along with fraction samples. Electrophoresis was performed at 25 mA/plate (stacking gel) or 40 mA/plate (running gel), until the bromphenol blue tracking dye migrated to the lower end of the gel (2.5–3 h). Gels were then stained for 60 minutes in 0.2% (w/v) Coomassie Brilliant Blue R250 dissolved in 50% (v/v) methanol, 10% (v/v) acetic acid, and finally destained in 50% (v/v) methanol, 10% (v/v) acetic acid.

SDS-PAGE analysis of pooled fractions A–E (defined above) obtained after 6FF Sepharose fractionation of the BOG extract of H. pylori cells indicates a range of enrichment with respect to H. pylori-specific and common antigens as shown in Table 1. The high molecular weight antigens (MW>200,000) of pools A and B appear on reduced PAGE gels as low molecular weight bands (MW<120,000) as a result of the digestion and reduction required for SDS-PAGE analysis.

TABLE 1

| Antigen MW (kd) | Pool A | B | C | D | E |
|---|---|---|---|---|---|
| H. pylori Specific | | | | | |
| 120 | — | — | 2* | — | — |
| 66 | 1 | 2 | 4 | — | — |
| 62, 59 | — | — | 3 | 0.5 | — |
| 52 | — | — | 2 | 1 | — |
| 31 | 0.5 | 2 | 3 | 1 | — |
| Common | | | | | |
| 89, 73 | — | — | 2 | — | — |
| 56 | 2 | 2 | 4 | 3 | 2 |
| 45, 42 | — | 0.5 | 2 | 0.5 | 0.5 |
| 29, 25 | — | 0.5 | 3 | 0 | 1 |
| 21, 16 | — | 2 | 2 | 2 | 1 |

*Relative intensity on 1–4 (highest) scale.

Table 1 indicates that pool C is relatively enriched in H. pylori-specific antigens.

The urease activity in each fraction was determined using a modification of the method of Mobley et al., Infect. Immun. (1986) 54:161–169, which involves measuring the pH change caused by ammonia generated by urease-catalyzed urea hydrolysis. A 50 μl aliquot of each fraction was added to 780 μl of urease substrate buffer (10 mM urea, 4.5 mM Sodium phosphate buffer (pH 6.8), 70 μg/ml phenol red) and the mixture incubated for 30 min at room temperature. Optical density of 100 μl aliquots was then measured at 550 nm using a MR 700 model microtiter plate reader (Dynatech Laboratories). Specific urease activity was expressed as a ratio of $OD_{550}/A_{280}$. FIG. 1 shows the 280-nm profile of a 6FF Sepharose fractionation of BOG extract and the specific urease activity of Pools B and C.

EXAMPLE 3

Comparison of Pool B, Pool C and other Antigens

In this example, Pool B, containing the majority of urease activity (fractions 20–33) and urease-depleted Pool C (fractions 34–52) were compared for ability to detect anti-H. pylori IgG antibodies in human sera, as described below.

Patient Serum Specimens

Serum and plasma specimens were collected at gastroenterology clinics from individuals who were defined as either H. pylori positive or negative, depending upon culture and histology results from gastric biopsies. The samples were further categorized by clinically diagnosed gastrointestinal signs.

H. pylori Flow-Through EIA Assay

The solid-phase subassembly consisted of an absorbent pad placed in a molded bottom casing, followed by 1 sq. inch of 8S Rayon and a 1.2μ Biodyne A nylon membrane. The nylon membrane was spotted with H. pylori extract diluted in antigen spotting solution followed by human IgG diluted in PBS containing sodium azide. The membranes were blocked with alkylated BSA solution for 30 minutes at room temperature, and then dried at 45° C. for 10–20 minutes. A molded top casing was placed on the treated nylon membrane with the spotted region in the center of the visual area, and sonically welded. A prefilter assembly was inserted into the welded units, placed in a foil pouch containing desiccant and heat sealed.

Test Procedure for Rapid Flow-Through EIA Assay

Using a 30-μl capillary dispensing device, a patient sample (either serum or plasma) was placed in a plastic cup with 150 μl of Sample Diluent. The diluted sample was added to the assay device described above and allowed to completely flow through the filter. Then, alkaline phosphatase-conjugated rabbit-antihuman IgG was added and allowed again to completely flow through. The filter was washed with 0.5 ml of wash solution, and 210 μl of a 3-indoxyl phosphate solution (a chromogenic substrate) was added to the cartridge. After incubation for 5 minutes, the membrane was washed completely to terminate the test. The immunoassay results were then interpreted within the next 15 minutes, using the following criteria:

A NEGATIVE RESULT was indicated by the appearance of a blue negative bar across the center of the membrane. A POSITIVE RESULT was indicated by the appearance of a solid blue circle superimposed over the control negative bar on the membrane. Absence of both the blue bar and solid blue circle indicated the test was uninterpretable, and the test should be repeated.

Suitability of Pool C of the *H. pylori* Antigen Extract to Detect Antibodies to *H. pylori* in Human Sera.

Rapid EIA was used on different antigen preparations to determine the frequency of false positive calls on human serum specimens. The antigen extracts used were: pools A and C of the BOG antigen extract; and sonicate and glycine extracts prepared as described above. The results are presented in Table 2.

TABLE 2

| Sample | Culture/ Histol. | Pool C | Pool A | Glycine | Sonicate |
|---|---|---|---|---|---|
| *H. pylori*-Negative Serum Specimens (Culture and Histology-confirmed) | | | | | |
| 4 | − | − | + | + | + |
| 6 | − | − | + | − | + |
| 7 | − | − | − | + | +/− |
| 8 | − | +/− | + | + | +/− |
| 10 | − | +/− | + | + | +/− |
| 13 | − | − | +/− | − | +/− |
| 14 | − | − | + | − | − |
| 15 | − | − | + | − | − |
| 16 | − | − | +/− | − | + |
| 22 | − | +/− | +/− | − | +/− |
| 32 | − | − | + | +/− | +/− |
| % False Positive: | 0% | 14% | 77% | 41% | 59% |
| *H. pylori*-Positive Serum Specimens (Culture and Histology-confirmed) | | | | | |
| 3 | + | + | + | + | + |
| 5 | + | + | + | + | + |
| 17 | + | + | + | + | + |
| 23 | + | + | + | + | + |
| Correct Calls: | | 100% for all tested extracts. | | | |

It can be seen that Pool C of the BOG antigen extract has the lowest frequency of false positives (14% versus 41 to 77% for the other antigen extracts).

Accuracy Correlation Study on Human Sera for Antibodies to *H. pylori* Using Pool C of BOG Antigen Extract One hundred eighty-three (183) serum and plasma specimens were collected at three gastroenterology clinics. Pool C of the BOG antigen extract was used in the rapid EIA assay. Test results were visually scored immediately following assay completion. Discordant specimens were tested by the Biometra microtiter ELISA test which detects IgG antibodies to *H. pylori*.

Correlation of the assay to culture and histology results is presented in Table 3.

TABLE 3

Rapid EIA Pool C Assay versus Culture/Histology

| | Culture/Histology Positive | Culture/Histology Negative |
|---|---|---|
| Rapid EIA Positive | 63 | 15 |
| Rapid EIA Negative | 3 | 102 |
| TOTAL: | 66 | 117 |

Pool C Sensitivity (% real positives correctly identified) = 95%
Pool C Specificity (% real negatives correctly identified) = 87%
Pool C Accuracy (% correct results) = 90%
Pool C PV (+) (reliability of positive result) = 81%
Pool C PV (−) (reliability of negative result) = 97%

Discordant specimen results were confirmed as infection-positive or negative using the Biometra ELISA test (Table 4).

TABLE 4

Discordant Sample Test Results

| Sample | Rapid EIA Result | Culture/Histology Result | Biometra ELISA Result |
|---|---|---|---|
| 52 | − | + | + |
| 56 | − | + | + |
| 59 | − | + | + |
| 3 | + | − | + |
| 5 | + | − | + |
| 32 | + | − | + |
| 46 | + | − | + |
| 50 | + | − | + |
| 62 | + | − | + |
| 73 | + | − | + |
| 91 | + | − | + |
| 105 | + | − | + |
| 117 | + | − | + |
| 119 | + | − | + |
| 140 | + | − | + |
| 167 | + | − | + |
| 173 | + | − | + |
| 174 | + | − | + |

Fourteen out of fifteen culture/histopathology-negative and rapid EIA-positive sera were confirmed positive in the Biometra ELISA. With these adjustments the Rapid EIA was shown to have a sensitivity and specificity of 96% and 99%, respectively (Table 5).

TABLE 5

Rapid EIA Pool C Assay versus Culture/Histology Adjusted for ELISA Results

| | Culture/Histology Positive | Culture/Histology Negative |
|---|---|---|
| Rapid EIA Positive | 77 | 1 |
| Rapid EIA Negative | 3 | 102 |
| TOTAL | 80 | 103 |

Corrected Pool C Sensitivity = 96%
Corrected Pool C Specificity = 99%
Corrected Pool C Accuracy = 98%
Corrected Pool C PV (+) = 99%
Corrected Pool C PV (−) = 97%

Comparison of a "Urease-enriched" Antigen Extract with Pool C for its Suitability in Detection of Antibodies to *H. pylori* in Human Sera.

A "urease-enriched" antigen preparation (Pool B) was prepared as described in U.S. Pat. No. 4,882,271 to Evans et al. and compared with the "urease-depleted" Pool C antigen as to their abilities to detect IgG antibodies against *H. pylori* in human sera in the rapid EIA test. Table 6 shows the results obtained with human serum specimens.

TABLE 6

Comparison of Pool B (Urease Antigen) with Pool C Using Rapid EIA Assay

| | H. pylori-Negative Sera | |
|---|---|---|
| Sample | Pool B (Urease) | Pool C |
| 4 | + | − |
| 6 | − | − |
| 7 | − | − |
| 8 | + | − |
| 9 | − | − |
| 10 | + | − |
| 11 | + | + |
| 13 | − | − |
| 14 | − | − |
| 15 | − | − |
| 16 | − | − |
| 19 | − | − |
| 21 | − | − |
| 25 | − | − |
| 63 | − | − |
| 64 | − | − |
| % false positives | 25% | 6% |

| | H. pylori-Positive Sera | |
|---|---|---|
| Sample | Urease | Pool C |
| 3 | + | + |
| 17 | + | + |
| 18 | + | + |
| 23 | + | + |
| 26 | + | + |
| 28 | + | + |
| 29 | + | + |
| 30 | + | + |
| % correct calls | 100% | 100% |

Table 6 demonstrates that the urease-depleted Pool C antigen has a lower frequency of false positives than the urease-enriched preparation of Evans (6% versus 25%, respectively).

EXAMPLE 4

Four different *H. pylori* antigen extracts (Pool A, pool C (urease-depleted), sonicated and glycine extracts) were compared in a microtiter ELISA format with culture and histology data on human serum specimens.

*H. pylori* EIA Microtiter Assay

Ninety-six-well, flat-bottomed, assembled microtiter plates were coated overnight at 4° C. with optimized concentrations of the four antigens. After antigen solution removal, the plates were air-dried and pouched. To perform immunoassays, the wells were rehydrated at room temperature with 300 μl of microtiter wash solution (PBS containing 0.05% (w/v) Tween 20 and 0.01% (w/v) Thimerosal). The liquid was then removed and the subsequent steps performed at 25° C. Serum specimens diluted 100-fold with PBS containing BSA were applied to wells (100 μl/well) and incubated for 30 minutes. The plates were washed five times with 300 μl of wash solution each and incubated for 30 minutes with peroxidase-conjugated rabbit-antihuman IgG. The plates were washed again five times with 300 μl of wash solution each and incubated for 15 minutes with a freshly prepared substrate solution consisting of 2-2' amino-di-(3-ethylbenzthiazaline sulfuric acid) diammonium salt (ABTS) and hydrogen peroxide. Reactions were stopped by the addition of 50 μl of 0.25M oxalic acid and absorbance was read at 410 nm with an MR 700 plate reader (Dynatech Laboratories).

The results presented in Table 7 indicate that Pool C, as compared to the other antigen preparations tested, is superior with regard to its specificity and sensitivity in identifying *H. pylori*-negative and *H. pylori*-positive human sera.

TABLE 7

Comparison of specificity and sensitivity of a microtiter ELISA assay for IgG antibodies in human sera using different *H. pylori* antigen preparations

| | Pool C (n = 29) | Pool A (n = 29) | Glycine (n = 48) | Sonicate (n = 33) |
|---|---|---|---|---|
| Specificity: | 93% | 72% | 73% | 64% |
| Sensitivity: | 100% | 100% | 100% | 100% |

Note:
1. n = number of histo-cytology determined *H. pylori*-negative sera tested.
2. Specificity is the ability to correctly detect *H. pylori*-negative sera as determined by histo-cytology.
3. Sensitivity is the ability to correctly detect *H. pylori*-positive sera as determined by histo-cytology.

We claim:

1. A composition comprising *Helicobacter pylori*-derived proteins useful to detect the presence of *H. pylori* antibodies
   wherein said *H. pylori*-derived proteins are obtainable by extracting intact *H. pylori* cells with n-octyl-β-D-glycopyranoside (BOG) to obtain an extract; subjecting said extract to sizing column chromatography to obtain fractions; and recovering urease-depleted fractions having a molecular weight of less than about 200 kD as determined by said sizing column chromatography;
   wherein said composition has a urease-specific activity of less than 0.34 $OD_{550}/A_{280}$ in a urease-catalyzed urease hydrolysis assay; and
   wherein the *H. pylori*-derived proteins in said composition, when denatured and reduced, are characterized by SDS PAGE to consist of antigens specific to *H. pylori* of molecular weights 120 kD; 66 kD; 62 kD; 59 kD; 52 kD; and 31 kD and common antigens of molecular weights 89 kD; 73 kD; 56 kD; 45 kD; 42 kD; 29 kD; 25 kD; 21 kD; and 16 kD; and
   wherein the amounts of antigens of 66 kD and of 56 kD are greater than the amounts of any of the remaining individual antigens set forth above.

2. A composition comprising *H. pylori*-derived proteins useful to detect the presence of *H. pylori* antibodies;
   wherein said composition has a urease-specific activity of less than 0.34 $OD_{550}/A_{280}$ in a urease-catalyzed assay, and the *H. pylori*-derived proteins in said composition, when denatured and reduced, are characterized by SDS PAGE to consist of antigens specific to *H. pylori* of molecular weights 120 kD; 66 kD; 62 kD; 59 kD; 52 kD; and 31 kD and common antigens of molecular weights 89 kD; 73 kD; 56 kD; 45 kD; 42 kD; 29 kD; 25 kD; 21 kD; and 16 kD;
   and wherein the amounts of antigens of 66 kD and 56 kD are greater than the amounts of any of the remaining individual antigens set forth above.

\* \* \* \* \*